(12) United States Patent
Park

(10) Patent No.: US 11,497,443 B2
(45) Date of Patent: Nov. 15, 2022

(54) SMART SHOE BASED ON RECOGNITION OF COMBINED WALKING ACTION AND DATA PROCESSING METHOD THEREOF

(71) Applicant: INFOWORKS INC., Seoul (KR)

(72) Inventor: Hyun-Ju Park, Seoul (KR)

(73) Assignee: INFOWORKS INC., Seoul (KR)

( * ) Notice: Subject to any disclaimer, the term of this patent is extended or adjusted under 35 U.S.C. 154(b) by 188 days.

(21) Appl. No.: 16/919,372

(22) Filed: Jul. 2, 2020

(65) Prior Publication Data

US 2020/0390396 A1 Dec. 17, 2020

(30) Foreign Application Priority Data

May 3, 2019 (KR) .......................... 10-2019-0052195

(51) Int. Cl.
| | | |
|---|---|---|
| *A61B 5/00* | (2006.01) | |
| *A61B 5/11* | (2006.01) | |
| *G16H 20/30* | (2018.01) | |
| *G16H 40/67* | (2018.01) | |
| *A43B 3/34* | (2022.01) | |

(52) U.S. Cl.
CPC .............. *A61B 5/6807* (2013.01); *A43B 3/34* (2022.01); *A61B 5/112* (2013.01); *A61B 5/1114* (2013.01); *A61B 5/7275* (2013.01); *G16H 20/30* (2018.01); *G16H 40/67* (2018.01); *A61B 2562/0219* (2013.01)

(58) Field of Classification Search
CPC .......... A61B 5/68–6802; A61B 5/6807; A61B 5/6829; A61B 5/1112–1115; A61B 5/112–1123; A61B 5/7275; A61B 2562/0219; G16H 20/30; G16H 40/67; A63B 2220/20–31; A63B 2220/40; G01B 21/22; G01C 19/00; G01P 15/00; A43B 3/34

See application file for complete search history.

(56) References Cited

U.S. PATENT DOCUMENTS

| | | | |
|---|---|---|---|
| 10,172,409 B1 * | 1/2019 | Andon .................... | G01S 19/19 |
| 2016/0179190 A1 * | 6/2016 | Lee ........................ | G01C 22/006 |
| | | | 345/156 |
| 2017/0225033 A1 * | 8/2017 | Czaja .................... | A43B 5/0405 |
| 2021/0401325 A1 * | 12/2021 | Fukushi ................. | A61B 5/112 |

FOREIGN PATENT DOCUMENTS

| | | |
|---|---|---|
| KR | 10-1250215 B1 | 4/2013 |
| KR | 10-2015-0049310 A | 5/2015 |
| KR | 10-1522466 B1 | 5/2015 |

* cited by examiner

*Primary Examiner* — Matthew Kremer
*Assistant Examiner* — Alyssa N Potter
(74) *Attorney, Agent, or Firm* — Sughrue Mion, PLLC

(57) ABSTRACT

Provided are a smart shoe and a data processing method thereof. The smart shoe includes: a stance phase measurement unit for, when one of two feet is set as a reference foot and a period during which the reference foot is taken off a ground and touches the ground again is set as a walking cycle, detecting acceleration and gyro in a stance phase in which the reference foot touches the ground; a swing phase measurement unit for detecting a difference between acceleration of the swing phase when the reference foot is taken off the ground and acceleration at the moment when the reference foot touches the ground; and a predict velocity update (PUPT) unit for obtaining and correcting a velocity of the stance phase condition.

9 Claims, 2 Drawing Sheets

SMART SHOE BASED ON RECOGNITION OF COMBINED WALKING ACTION AND DATA PROCESSING METHOD THEREOF

CROSS-REFERENCE TO RELATED APPLICATION

This application claims the benefit of Korean Patent Application No. 10-2019-0052195, filed on May 3, 2019, in the Korean Intellectual Property Office, the disclosure of which is incorporated herein in its entirety by reference.

BACKGROUND

1. Field

The present invention relates to a smart shoe and a data processing method thereof, and more particularly, to a smart shoe based on recognition of a combined walking action and a data processing method thereof, wherein a position and a direction of a pedestrian can be accurately estimated by correcting a zero velocity while modifying a velocity of a stopped state in a process of recognizing a walking action.

2. Description of Related Art

Generally, in Pedestrian Dead Reckoning (PDR) technologies, INS-EKF-ZUPT (IEZ) or Step and Heading System (SHS) is used. IEZ has a disadvantage that errors increase over time due to the accumulation of errors occurring upon walking, like many PDR technologies. SHS operates in a state in which an inertial sensor is attached to a waist or the like and has a limitation in accurately measuring the stride and step.

Therefore, in PDR technologies, correcting errors, that is, reducing errors may be a very important factor in determining the accuracy of the technology. In the related field, research has focus on reducing an error range by subdividing a walking motion and applying an algorithm suitable for the subdivided walking motion through sensor values.

However, PDR commonly uses Zero velocity UPdaTe (ZUPT) that corrects a velocity in a standing state, that is, a stopped state, to zero and uses the corrected velocity as a filter value. Even when the walking is stopped, a standing motion is not reflected to a walking motion. Therefore, there is a fundamental limitation in reducing an error range in a PDR field. There is a need to conduct research for solving this problem.

PRIOR ART DOCUMENT

Patent Document (Patent Document 0001) Korean Patent Registration No. 10-1250215
(Patent Document 0002) Korean Patent Registration No. 10-1522466

SUMMARY

The present invention has been made in an effort to solve the problems of the related art, and an object of the present invention is to provide a smart shoe based on recognition of a combined walking action and a data processing method thereof, wherein a position and a direction of a pedestrian can be accurately estimated by recognizing a walking action even in a place where position information cannot be received and correcting a velocity of a stopped state and a zero velocity.

In order to achieve the object, the present invention includes: a stance phase measurement unit for, when one of two feet is set as a reference foot and a period during which the reference foot is taken off a ground and touches the ground again is set as a walking cycle, detecting acceleration and gyro in a stance phase in which the reference foot touches the ground; a swing phase measurement unit for detecting a difference between acceleration of the swing phase when the reference foot is taken off the ground and acceleration at the moment when the reference foot touches the ground; and a predict velocity update (PUPT) unit for obtaining and correcting a velocity of the stance phase condition.

The stance phase measurement unit determines a walking condition through magnitudes of acceleration and gyro, and a variance value. In particular, the stance phase measurement unit determines the walking condition with a threshold value through at least one of energy for acceleration, product, sum, variance value, and magnitude of gyro.

The stance phase measurement unit obtains energy (Energy) for acceleration and an energy variance value ($Var_{Energy}$) by using Equation 1, obtains the product (Product) and a product variance value ($Var_{Product}$) by using Equation 2, obtains the sum (Sum) and a sum variance value ($Var_{sum}$) by using Equation 3, obtains a norm (Norm Gyro) for the gyro and a norm variance value ($Var_{Ng}$) by using Equation 4, and determines a stance walking condition ($Condition_{stance}$) by using Equation 5:

$$\text{Energy} = (a_x/g)^2 + (a_z/g)^2, \quad \text{Equation 1}$$
$$Var_{Energy} = \text{var}(\text{Energy}(Buffer_k))$$
$$Condition_{Ve} = \begin{cases} 1 & V_e < th \\ 0 & \text{otherwise} \end{cases}$$

$$\text{Product} = (a_x/g) * (a_z/g), \quad \text{Equation 2}$$
$$Var_{Product} = \text{var}(\text{Product}(Buffer_k))$$
$$Condition_{Vp} = \begin{cases} 1 & V_p < th \\ 0 & \text{otherwise} \end{cases}$$

$$\text{Sum} = (a_x + a_z)/g, \quad \text{Equation 3}$$
$$Var_{Sum} = \text{var}(\text{Sum}(buffer_k))$$
$$Condition_{Vs} = \begin{cases} 1 & V_s < th \\ 0 & \text{otherwise} \end{cases}$$

$$\text{Norm Gyro} = \sqrt{G_y^2}, \quad \text{Equation 4}$$
$$Var_{Ng} = \text{var}(Norm_G(buffer_k))$$
$$Condition_{Ng} = \begin{cases} 1 & Var_{Ng} < th \\ 0 & \text{otherwise} \end{cases}$$
$$Condition_{Gy} = \begin{cases} 1 & \text{abs}(G_y) < th \\ 0 & \text{otherwise} \end{cases}$$

$$Condition_{stance} = Condition_{Ve} \cdot Condition_{Vp} \cdot \quad \text{Equation 5}$$
$$Condition_{Vs} \cdot Condition_{Ng} \cdot Condition_{Gy}$$

(wherein, $a_x$ is a shoe progress direction, $a_z$ is a direction perpendicular to the ground, g is a gravitational acceleration, $buffer_k$ is a sensor data stored for a certain time and refers to a set of data from an arbitrary past k time point from a present, $V_e$ is $Var_{Energy}$, $V_P$ is $Var_{Product}$, $V_s$ is $Var_{sum}$, $G_y$ is a y-axis value of the gyro, th is a threshold value, a walking condition ($Condition_{stance}$) is assumed to be a stance phase when the product of Condition$_{Ve}$, Condition$_{Vp}$, Condition$_{Vs}$, Condition$_{Ng}$, and Condition$_{Gy}$ is 1).

In addition, the swing phase measurement unit detects an acceleration difference (Diff$_{az}$) by using Equation 6 and determines a swing phase walking condition (Condition$_{Heel}$) by using Equation 7:

$$Diff_{a_z} = Diff(a_z - a_z^{prev}) \quad \text{Equation 6}$$

$$Condition_{Diff} = \begin{cases} 1 & Diff_{a_z} < -th \\ 0 & \text{otherwise} \end{cases}$$

$$Condition_{time} = \begin{cases} 1 & time > th \\ 0 & \text{otherwise} \end{cases}$$

$$Condition_{Heel} = Condition_{Diff} \cdot Condition_{time} \quad \text{Equation 7}$$

(wherein, $a_z$ is a shoe progress direction perpendicular to the ground, $a_z^{prev}$ is a direction perpendicular to a previous ground, and th is a threshold value).

The PUPT unit uses a sensor to set a position of a shoe sole touching the ground and uses the position of the shoe sole as a correction value. When a phase changes from the stance phase to the swing phase during walking, a specific contact point of the shoe touching the ground is checked through calculation of sensor data, and an instantaneous velocity of the shoe obtained by multiplying a rotational angle and a force (lever arm vector) applied to the obtained contact point is applied to the PUPT unit.

In particular, the PUPT unit sets a position of a shoe sole according to condition 1, obtains a vector (rb) between the sensor and the shoe sole by using Equation 8, obtains a velocity value (Vb) to be corrected by using Equation 9, and obtains an estimated acceleration (Acc) by using Equation 10:

$$Contact_x = \begin{cases} Value_1 & pitch > th_1 \\ Value_2 & pitch < -th_2 \\ Value_3 & \text{otherwise} \end{cases} \quad \text{Condition 1}$$

$$Contact_y = \begin{cases} Value_1 & roll > th_1 \\ Value_2 & roll < -th_2 \\ Value_3 & \text{otherwise} \end{cases}$$

$$r_x^b = S_x^i - Contact_x, \quad \text{Equation 8}$$
$$r_y^b = S_y^i - Contact_y,$$
$$r_z^b = th$$

$$V^b = Gyro \times r^b \quad \text{Equation 9}$$

$$Acc = \text{skewsymm}(Diff_{gyro}) + \quad \text{Equation 10}$$
$$\text{skewsymm}(gyro) \cdot \text{skewsymm}(gyro) \cdot r^b - C^* \cdot [0 \ 0 \ g]$$

(wherein, Value$_1$ to Value$_3$ represent three contact points between the shoe sole and the ground which are divided by two thresholds (th$_1$ and th$_2$), pitch represents the rotation direction around the x-axis, roll represents the rotation about the y-axis, r is a lever arm vector which refers to the torque vector transmitted between the rotating body and the central axis, b represents the body frame, S (Skewsymm) represents an antisymmetric matrix, i represents the inertial frame, th represents the threshold, $V^b$ represents the instantaneous velocity of the body, gyro represents the direction angle, C represents a direction cosine matrix (DCM) which is a matrix having a rotation angle value of a rotated object and refers to a posture, C* represents a DCM transpose matrix, and g represents the gravitational acceleration.)

In addition, a walking analysis server for collecting walking data according to walking motions and shoe sizes different for each pedestrian and analyzing a compensation value through deep learning filters the velocity of the stance phase condition corrected by the PUPT unit.

The present invention includes: a stance phase predicting step in which the stance phase measurement unit predicts the stride and azimuth angle through energy for acceleration, product, sum, variance value, and magnitude of gyro; a swing phase detecting step in which the swing phase determination unit detects a difference between the acceleration of the swing phase and the moment upon touching the ground; and a position estimating step in which the PUPT unit estimates a stride and an azimuth angle by correcting the velocity of the stance phase and estimating the position.

DETAILED DESCRIPTION

The terms or words used in the present specification and the claims should not be construed as being limited to ordinary or dictionary meanings. The inventors should be construed as meanings and concepts consistent with the technical idea of the present invention, based on the principle that the concept of the terms can be appropriately defined in order to explain their invention in the best way.

Therefore, the configurations shown in the embodiments and drawings described in the present specification are only the most preferred embodiments of the present invention and do not represent all of the technical spirit of the present invention. Therefore, it should be understood that there may be various equivalents and modifications that can replace them at the time of filing.

Hereinafter, a smart shoe based on recognition of a combined walking action and a data processing method thereof according to the present invention will be described with reference to the accompanying drawings.

Figure 1:
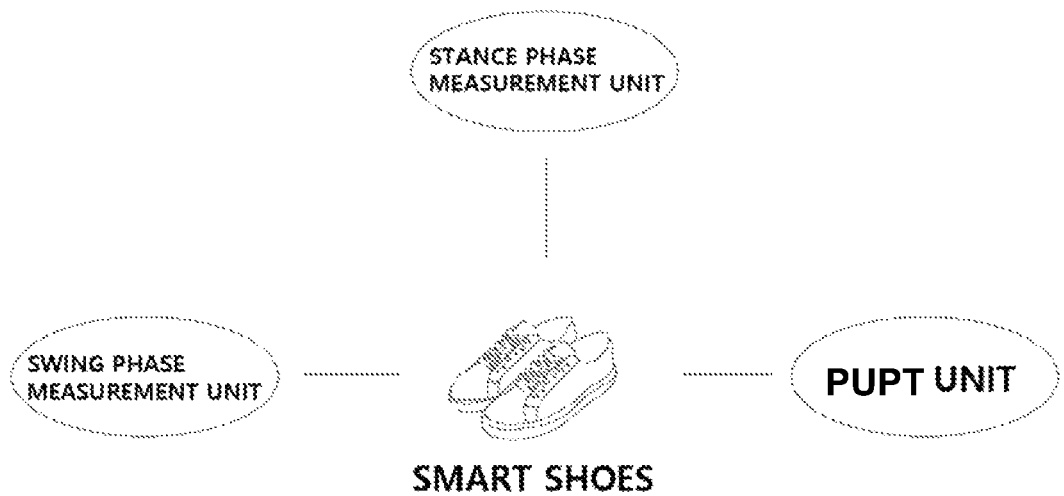
FIG. 1 is a block diagram illustrating main elements of a smart shoe based on recognition of a combined walking action, according to the present invention.
Figure 2:
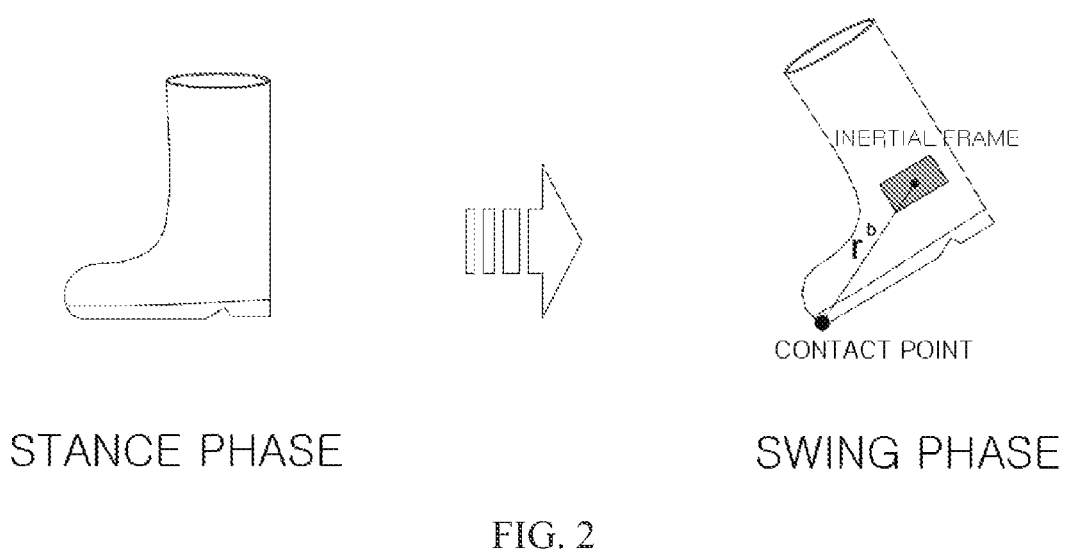
FIG. 2 is a diagram schematically illustrating multiple contact point modeling of the smart shoe based on the recognition of the combined walking action, according to the present invention.

FIG. 1 is a block diagram illustrating main elements of a smart shoe based on recognition of a combined walking action, according to the present invention, and FIG. 2 is a diagram schematically illustrating multiple contact point modeling of the smart shoe based on the recognition of the combined walking action, according to the present invention.

The present invention basically includes a stance phase measurement unit, a swing phase measurement unit, and a Predict velocity UPdaTe (PUPT) unit.

More specifically, the present invention includes: a stance phase measurement unit for, when one of two feet is set as a reference foot and a period during which the reference foot is taken off the ground and touches the ground again is set as a walking cycle, detecting acceleration and gyro in a stance phase in which the reference foot touches the ground;

a swing phase measurement unit for detecting a difference between acceleration of the swing phase when the reference foot is taken off the ground and acceleration at the moment when the reference foot touches the ground; and a PUPT unit for obtaining and correcting a velocity of a stance phase condition.

When the reference foot is set as the right foot, the walking period means the moment when the left foot is stepped on the ground in a state in which the right foot is stepped on the ground, and then the right foot heel touches the ground again. In the general sense, the walking period means two steps.

In addition, the stance phase means a period during which the foot touches the ground with respect to the reference foot. Specifically, the stance phase may be divided into heel strike, foot flat, mid stance, heel off, and toe off. The swing phase means a period during which the foot is taken off the ground. Specifically, the swing phase may be divided into acceleration, mid swing, and deceleration.

The stance phase measurement unit determines the walking condition through magnitudes of acceleration and gyro, and a variance value. In particular, the walking condition is determined with a threshold value through energy for acceleration, product, sum, variance value, and magnitude of gyro.

More specifically, the stance phase measurement unit may obtains the stance phase measurement unit obtains energy (Energy) for acceleration and an energy variance value (Var$_{Energy}$) by using Equation 1, obtains the product (Product) and a product variance value (Var$_{Product}$) by using Equation 2, obtains the sum (Sum) and a sum variance value (Var$_{sum}$) by using Equation 3, obtains a norm (Norm Gyro) for the gyro and a norm variance value (Var$_{Ng}$) by using Equation 4, and determines a stance walking condition (Condition$_{stance}$) by using Equation 5:

$$\text{Energy} = (a_x/g)^2 + (a_z/g)^2, \quad \text{Equation 1}$$
$$\text{Var}_{Energy} = \text{var}(\text{Energy}(Buffer_k))$$
$$\text{Condition}_{Ve} = \begin{cases} 1 & V_e < th \\ 0 & \text{otherwise} \end{cases}$$

$$\text{Product} = (a_x/g) * (a_z/g), \quad \text{Equation 2}$$
$$\text{Var}_{Product} = \text{var}(\text{Product}(Buffer_k))$$
$$\text{Condition}_{Vp} = \begin{cases} 1 & V_p < th \\ 0 & \text{otherwise} \end{cases}$$

$$\text{Sum} = (a_x + a_z)/g, \quad \text{Equation 3}$$
$$\text{Var}_{Sum} = \text{var}(\text{Sum}(buffer_k))$$
$$\text{Condition}_{Vs} = \begin{cases} 1 & V_s < th \\ 0 & \text{otherwise} \end{cases}$$

$$\text{Norm Gyro} = \sqrt{G_y^2}, \quad \text{Equation 4}$$
$$\text{Var}_{Ng} = \text{var}(Norm_G(buffer_k))$$
$$\text{Condition}_{Ng} = \begin{cases} 1 & Var_{Ng} < th \\ 0 & \text{otherwise} \end{cases}$$
$$\text{Condition}_{Gy} = \begin{cases} 1 & abs(G_y) < th \\ 0 & \text{otherwise} \end{cases}$$

$$\text{Condition}_{stance} = \text{Condition}_{Ve} \cdot \text{Condition}_{Vp} \cdot \quad \text{Equation 5}$$
$$\text{Condition}_{Vs} \cdot \text{Condition}_{Ng} \cdot \text{Condition}_{Gy}$$

(wherein, $a_x$ is a shoe progress direction, $a_z$ is a direction perpendicular to the ground, g is a gravitational acceleration, buffer$_k$ is a sensor data stored for a certain time and refers to a set of data from an arbitrary past k time point from a present, $V_e$ is Var$_{Energy}$, $V_p$ is Var$_{Product}$, $V_s$ is Var$_{sum}$, $G_y$ is a y-axis value of the gyro, th is a threshold value, a walking condition (Condition$_{stance}$) is assumed to be a stance phase when the product of Condition$_{Ve}$, Condition$_{Vp}$, Condition$_{Vs}$, Condition$_{Ng}$, and Condition$_{Gy}$ is 1).

Equations 1 to 5 will be described in detail. First, in relation to acceleration, the reference of the acceleration direction may be determined in the initial alignment process of the gait and the reference of the gyro x, y, and z directions is identical to the acceleration ($a_x$: direction in which the shoe moves, $a_y$: direction perpendicular to the direction in which the shoe moves outward, $a_z$: direction perpendicular to the ground). Second, in relation to the variance value, raw data collected for detecting the stance phase is processed and the presence or absence of the stance phase is detected by using the variance of the set (Buffer$_k$) of processed data.

In addition, the swing phase measurement unit may detect a late swing phase changing from the swing phase to the stance phase, may detect the late swing phase through the acceleration difference that occurs when touching the ground, and may detect an acceleration difference (Diff$_{az}$) by using Equation 6 and determine a swing phase walking condition (Condition$_{Heel}$) by using Equation 7:

$$Diff_{a_z} = Diff(a_z - a_z^{prev}) \quad \text{Equation 6}$$
$$\text{Condition}_{Diff} = \begin{cases} 1 & Diff_{a_z} < -th \\ 0 & \text{otherwise} \end{cases}$$
$$\text{Condition}_{time} = \begin{cases} 1 & time > th \\ 0 & \text{otherwise} \end{cases}$$

$$\text{Condition}_{Heel} = \text{Condition}_{Diff} \cdot \text{Condition}_{time} \quad \text{Equation 7}$$

(wherein, $a_z$ is a shoe progress direction perpendicular to the ground, $a_z^{prev}$ is a direction perpendicular to a previous ground, and th is a threshold value).

Equations 6 and 7 will be described in detail. When detecting the swing phase, two conditions are considered. The first condition is whether the foot moves vertically (when the magnitude of the z-axis acceleration is significantly different from the previous value, it may be interpreted that the foot is lowered or lifted). The second condition is whether the time passed (when the value is continuously measured, the difference in the z-axis acceleration value may appear smaller than the threshold value, and thus, the minimum time interval is set so that the acceleration in the z-axis direction is perpendicular to the ground, and this is used to indicate the movement attribute in the z-axis (height) direction.

The swing phase measurement unit considers the difference between the previous z-axis acceleration value and the current acceleration value. Since there is the minimum time between the stance phase and the swing phase, the late swing phase may be detected when the minimum reference time has elapsed after the stance phase and the swing phase.

A conventional INS-EKF-ZUPT (IEZ) technology uses a ZUPT algorithm that considers the velocity of the stance phase condition to be zero. However, even in the stance phase condition, the movement has a certain non-zero velocity due to the walking characteristics. The error may be reduced by obtaining and correcting the velocity of the stance phase condition through the PUPT unit. Since the stance phase may appear after the late swing phase, the error may be reduced by estimating the velocity after the late swing phase in which the foot touches the ground. Therefore, PUPT is applied by multiple contact point modeling through a sensor provided at the shoe sole in order to obtain the velocity after the late swing phase, that is, after the swing phase.

To this end, the PUPT unit uses the sensor to set the position of the shoe sole touching the ground and uses the position of the shoe sole as a correction value. When the phase changes from the stance phase to the swing phase during walking, a specific contact point of the shoe touching the ground is checked through the calculation of sensor data, and an instantaneous velocity of the shoe obtained by multiplying the rotational angle and the force (lever arm vector) applied to the obtained contact point is applied to the PUPT unit.

In particular, the PUPT unit sets the position of the shoe sole according to the following condition 1, obtains the vector $r^b$ between the sensor and the shoe sole by using Equation 8, obtains the velocity value $V^b$ to be corrected by using Equation 9, and obtains the estimated acceleration Acc by using Equation 10:

$$Contact_x = \begin{cases} Value_1 & pitch > th_1 \\ Value_2 & pitch < -th_2 \\ Value_3 & otherwise \end{cases} \quad \text{Condition 1}$$

$$Contact_y = \begin{cases} Value_1 & roll > th_1 \\ Value_2 & roll < -th_2 \\ Value_3 & otherwise \end{cases}$$

$$r_x^b = S_x^i - Contact_x, \quad \text{Equation 8}$$
$$r_y^b = S_y^i - Contact_y,$$
$$r_z^b = th$$

$$V^b = Gyro \times r^b \quad \text{Equation 9}$$

$$Acc = skewsymm(Diff_{gyro}) + \quad \text{Equation 10}$$
$$skewsymm(gyro) \cdot skewsymm(gyro) \cdot r^b - C^* \cdot [\,0 \;\; 0 \;\; g\,]$$

(wherein, $Value_1$ to $Value_3$ represent three contact points between the shoe sole and the ground which are divided by two threshold values ($th_1$ and $th_2$), pitch represents the rotation direction around the x-axis, roll represents the rotation about the y-axis, r is a lever arm vector which refers to the torque vector transmitted between the rotating body and the central axis, b represents the body frame, S (Skewsymm) represents an antisymmetric matrix, i represents the inertial frame, th represents the threshold value, $V^b$ represents the instantaneous velocity of the body, gyro represents the direction angle, C represents a direction cosine matrix (DCM) which is a matrix having a rotation angle value of a rotated object and refers to a posture, $C^*$ represents a DCM transpose matrix, and g represents the gravitational acceleration.)

Condition 1 and Equations 8 to 10 will be described in detail. In the present invention, three contact points are assumed as an example of a modeling while using the method of reducing the positioning error of the PDR through the multiple contact point shoe modeling, and the position is estimated. When the shoe touches the ground, gyro data is used to determine which contact point the shoe touches among the three contact points. The torque transmitted between the rotating body and the central axis is lever-arm, and lever-arm $r_x^b$ is obtained by subtracting the value taken from multiple contact point shoe modeling in the antisymmetric matrix of acceleration component values for the x-axis of the inertial sensor (for reference, the central axis=inertial sensor: $s_x^i$, point of force applied to the rotating body: indicated as $contact_x$).

When detecting the swing phase, two conditions are considered. The first condition is whether the foot moves vertically (when the magnitude of the z-axis acceleration is significantly different from the previous value, it may be interpreted that the foot is lowered or lifted). The second condition is whether the time passed (when the value is continuously measured, the difference in the z-axis acceleration value may appear smaller than the threshold value, and thus, the minimum time interval is set so that the acceleration in the z-axis direction is perpendicular to the ground, and this is used to indicate the movement attribute in the z-axis (height) direction.

According to the PUPT unit as described above, when the contact points are generalized as one contact point, it is based on the assumption that general gait is measured, and thus it is difficult to apply to various gaits (crawling, sidling, etc.). However, due to the application of the multiple contact point modeling to the shoe, various walking postures such as general walking (heel first touches the ground when walking), crawling (the front end of the foot first touches the ground in a state of crawling on hands), sidling (the side or the bottom of the foot first touches the ground in a sideways movement), etc. may be checked.

Hereinafter, matters to be considered according to different shoe sizes and walking styles for each pedestrian will be described.

1) Magnitude of Velocity Compensation According to Shoe Size

The PUPT unit detects the position of the shoe touched in the late swing phase and corrects the velocity accordingly. However, the velocity correction value has to be changed because the vector size between the sensor and the sole contact point is different for each pedestrian according to the shoe size.

2) Problems Regarding Positions of Contact Points According to Pedestrian's Walking Style Since the contact points may be different according to the pedestrian's walking style, it is necessary to perform fine adjustment according to the pedestrian's style at the positions of the contact points divided according to the walking motion.

In the present invention, in order to solve the above problems, the walking analysis server for collecting walking data according to walking motions and shoe sizes different for each pedestrian and analyzing the compensation value through deep learning filters the velocity of the stance phase condition corrected by the PUPT unit. For example, in the process of receiving pedestrian's walking data through sensors for positioning of the pedestrians and performing PDR calculation, the compensation value obtained by performing deep learning while collecting big data is applied to the filter to calculate more accurate individual PDR conditions.

For reference, it is obvious that the smart shoe according to the present invention may include a communication module to transmit data calculated by each component, that is, walking data checkable for the position, direction, etc. of the pedestrian, to the pedestrian's own terminal and the walking analysis server. As described above, it is well known to the art and various fields to transmit data to the terminal by wire or wireless through the communication module. Therefore, a detailed description thereof will be omitted.

Figure 3:
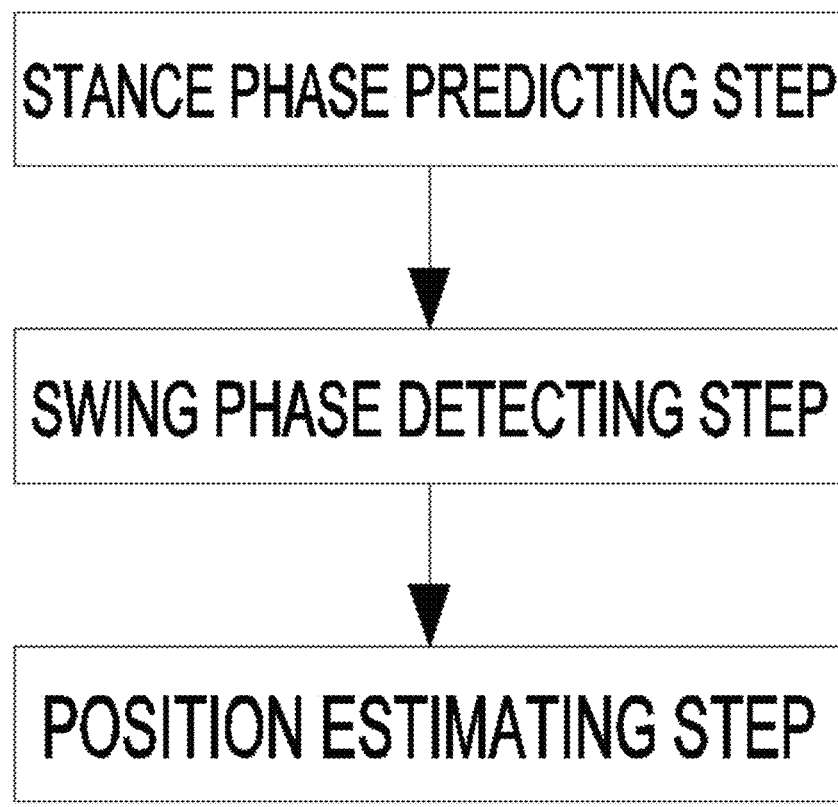
FIG. 3 is a data processing method of the shoe based on the recognition of the combined walking action, according to the present invention.

FIG. 3 is a data processing method of the shoe based on the recognition of the combined walking action, according to the present invention.

The present invention includes: a stance phase predicting step in which the stance phase measurement unit predicts the stride and azimuth angle through energy for acceleration, product, sum, variance value, and magnitude of gyro; a swing phase detecting step in which the swing phase determination unit detects the difference between the acceleration of the swing phase and the moment upon touching the ground; and a position estimating step in which the PUPT unit estimates the stride and azimuth angle by correcting the velocity of the stance phase and then estimating the position.

According to the present invention, since the velocity can be modified and the zero velocity can be corrected even in a place where position information cannot be received, the measurement error in the walking condition can be minimized and the position and the direction of the pedestrian can be more accurately estimated. For example, even when a firefighter enters a room where position information cannot be received, the position of the firefighter can be detected in real time by checking the walking condition through the smart shoe. As a result, the positions of a plurality of firefighters can be efficiently monitored.

In the smart shoe based on recognition of a combined walking action and the data processing method thereof, the position and the direction of the pedestrian can be accurately estimated by recognizing the walking action even in a place where position information cannot be received and correcting the velocity of the stopped state and the zero velocity.

For example, even when a firefighter enters a room where position information cannot be received, the position of the firefighter can be detected in real time by checking the walking state through the shoe. As a result, the positions of the plurality of firefighters can be efficiently monitored.

Specific shapes and directions have been mainly described in describing the present invention with reference to the accompanying drawings. However, the present invention can be variously modified and changed by those of ordinary skill in the art and such modifications and changes should be construed as falling within the scope of the present invention.

What is claimed is:

1. A smart shoe based on recognition of a combined walking action, the smart shoe comprising:
   a stance phase measurement unit for, when one of two feet is set as a reference foot and a period during which the reference foot is taken off a ground and touches the ground again is set as a walking cycle, detecting acceleration and gyro in a stance phase in which the reference foot touches the ground;
   a swing phase measurement unit for detecting a difference between acceleration of a swing phase when the reference foot is taken off the ground and acceleration at a moment when the reference foot touches the ground; and
   a predict velocity update (PUPT) unit for obtaining and correcting a velocity of the stance phase,
   wherein the swing phase measurement unit detects an acceleration difference ($Diff_{a_z}$) by using Equation 1 and determines a swing phase walking condition ($Condition_{Heel}$) by using Equation 2:

$$Diff_{a_z} = Diff(a_z - a_z^{prev}) \quad \text{Equation 1}$$

$$Condition_{Diff} = \begin{cases} 1 & Diff_{a_z} < -th \\ 0 & \text{otherwise} \end{cases}$$

$$Condition_{time} = \begin{cases} 1 & time > th \\ 0 & \text{otherwise} \end{cases}$$

$$Condition_{Heel} = Condition_{Diff} \cdot Condition_{time} \quad \text{Equation 2}$$

wherein, $a_z$ is a shoe progress direction perpendicular to the ground, $a_{prev}^z$ is a direction perpendicular to a previous ground, and th is a threshold value.

2. The smart shoe of claim 1, wherein the stance phase measurement unit determines a walking condition through magnitudes of acceleration and gyro, and a variance value.

3. The smart shoe of claim 2, wherein the stance phase measurement unit determines the walking condition by using the threshold value based on at least one of energy for acceleration, product, sum, variance value, and magnitude of gyro.

4. The smart shoe of claim 1, wherein the PUPT unit uses a sensor to set a position of a shoe sole touching the ground and uses the position of the shoe sole as a correction value.

5. The smart shoe of claim 4, wherein, when a phase changes from the stance phase to the swing phase during walking, a specific contact point of the shoe touching the ground is checked through calculation of sensor data, and an instantaneous velocity of the shoe obtained by multiplying a rotational angle and a force applied to the obtained contact point is applied to the PUPT unit.

6. The smart shoe of claim 1, wherein a walking analysis server for collecting walking data according to walking motions and shoe sizes different for each pedestrian and analyzing a compensation value through deep learning filters the velocity of the stance phase corrected by the PUPT unit.

7. A data processing method of the smart shoe according to claim 1, the data processing method comprising:
   a stance phase predicting step in which the stance phase measurement unit predicts a stride and an azimuth angle based on energy for acceleration, product, sum, variance value, and magnitude of gyro;
   a swing phase detecting step in which the swing phase measurement unit detects the difference between the acceleration of the swing phase and the acceleration at the moment when the reference foot touches the ground; and
   a position estimating step in which the PUPT unit estimates the stride and the azimuth angle by correcting the velocity of the stance phase and estimating a position of a shoe sole.

8. A smart shoe based on recognition of a combined walking action, the smart shoe comprising:
   a stance phase measurement unit for, when one of two feet is set as a reference foot and a period during which the reference foot is taken off a ground and touches the ground again is set as a walking cycle, detecting acceleration and gyro in a stance phase in which the reference foot touches the ground;
   a swing phase measurement unit for detecting a difference between acceleration of a swing phase when the reference foot is taken off the ground and acceleration at a moment when the reference foot touches the ground; and
   a predict velocity update (PUPT) unit for obtaining and correcting a velocity of the stance phase, wherein the stance phase measurement unit obtains energy (Energy) for acceleration and an energy variance value ($Var_{Energy}$) by using Equation 1, obtains a product (Product) and a product variance value ($Var_{Product}$) by using Equation 2, obtains a sum (Sum) and a sum variance value ($Var_{sum}$) by using Equation 3, obtains a norm (Norm Gyro) for the gyro and a norm variance value ($Var_{Ng}$) by using Equation 4, and determines a stance walking condition ($Condition_{stance}$) by using Equation 5:

$$Energy = (a_x/g)^2 + (a_z/g)^2,$$
$$Var_{Energy} = var(Energy(Buffer_k))$$
$$Condition_{Ve} = \begin{cases} 1 & V_e < th \\ 0 & otherwise \end{cases}$$
Equation 1

$$Product = (a_x/g)*(a_z/g),$$
$$Var_{Product} = var(Product(Buffer_k))$$
$$Condition_{Vp} = \begin{cases} 1 & V_p < th \\ 0 & otherwise \end{cases}$$
Equation 2

$$Sum = (a_x + a_z)/g,$$
$$Var_{Sum} = var(Sum(buffer_k))$$
$$Condition_{Vs} = \begin{cases} 1 & V_s < th \\ 0 & otherwise \end{cases}$$
Equation 3

$$Norm\ Gyro = \sqrt{G_y^2},$$
$$Var_{Ng} = var(Norm_G(buffer_k))$$
$$Condition_{Ng} = \begin{cases} 1 & Var_{Ng} < th \\ 0 & otherwise \end{cases}$$
$$Condition_{Gy} = \begin{cases} 1 & abs(G_y) < th \\ 0 & otherwise \end{cases}$$
Equation 4

$$Condition_{stance} = Condition_{Ve} \cdot Condition_{Vp} \cdot Condition_{Vs} \cdot Condition_{Ng} \cdot Condition_{Gy}$$
Equation 5 wherein, ($a_x$ is a shoe progress direction, $a_z$ is a direction perpendicular to the ground, g is a gravitational acceleration, $buffer_k$ is a sensor data stored for a certain time and refers to a set of data from an arbitrary past k time point from a present, $V_e$ is $Var_{Energy}$, $V_p$ is $Var_{Product}$, $V_s$ is $Var_{sum}$, $G_y$ is a y-axis value of the gyro, th is a threshold value, and the stance walking condition ($Condition_{stance}$) is assumed to be the stance phase based on a product of $Condition_{Ve}$, $Condition_{Vp}$, $Condition_{Vs}$, $Condition_{Ng}$, and $Condition_{Gy}$ being 1.

9. A smart shoe based on recognition of a combined walking action, the smart shoe comprising:
a stance phase measurement unit for, when one of two feet is set as a reference foot and a period during which the reference foot is taken off a ground and touches the ground again is set as a walking cycle, detecting acceleration and gyro in a stance phase in which the reference foot touches the ground;
a swing phase measurement unit for detecting a difference between acceleration of a swing phase when the reference foot is taken off the ground and acceleration at a moment when the reference foot touches the ground; and
a predict velocity update (PUPT) unit for obtaining and correcting a velocity of the stance phase,
wherein the PUPT unit uses a sensor to set a position of a shoe sole touching the ground and uses the position of the shoe sole as a correction value, and
wherein the PUPT unit sets the position of the shoe sole according to condition 1, obtains a vector ($r^b$) between the sensor and the shoe sole by using Equation 8, obtains a velocity value ($V^b$) to be corrected by using Equation 9, and obtains an estimated acceleration (Acc) by using Equation 10:

$$Contact_x = \begin{cases} Value_1 & pitch > th_1 \\ Value_2 & pitch < -th_2 \\ Value_3 & otherwise \end{cases}$$
Condition 1

$$Contact_y = \begin{cases} Value_1 & roll > th_1 \\ Value_2 & roll < -th_2 \\ Value_3 & otherwise \end{cases}$$

$$r_x^b = S_x^i - Contact_x,$$
$$r_y^b = S_y^i - Contact_y,$$
$$r_z^b = th$$
Equation 8

$$V^b = Gyro \times r^b$$
Equation 9

$$Acc = skewsymm(Diff_{gyro}) + skewsymm(gyro) \cdot skewsymm(gyro) \cdot r^b - C^* \cdot [0\ 0\ g]$$
Equation 10 wherein, ($Value_1$ to $Value_3$ represent three contact points between the shoe sole and the ground which are divided by two thresholds ($th_1$ and $th_2$), pitch represents a rotation direction around an x-axis, roll represents a rotation direction about a y axis, r is a lever arm vector which refers to a torque vector transmitted between a rotating body and a central axis, b represents a body frame, S (Skewsymm) represents an antisymmetric matrix, i represents an inertial frame, th represents a threshold, $V^b$ represents an instantaneous velocity of the rotating body, gyro represents a direction angle, C represents a direction cosine matrix (DCM) which is a matrix having a rotation angle value of a rotated object and refers to a posture, $C^*$ represents a DCM transpose matrix, and g represents a gravitational acceleration.

* * * * *